United States Patent
Shedlock et al.

(10) Patent No.: US 9,086,496 B2
(45) Date of Patent: Jul. 21, 2015

(54) FEEDBACK MODULATED RADIATION SCANNING SYSTEMS AND METHODS FOR REDUCED RADIOLOGICAL FOOTPRINT

(71) Applicant: Varian Medical Systems, Inc., Palo Alto, CA (US)

(72) Inventors: Daniel Shedlock, Knoxville, TN (US); Timothy R. Fox, Chicago, IL (US); Josh Star-Lack, Palo Alto, CA (US); Richard E. Colbeth, Los Altos, CA (US); Gary Virshup, Cupertino, CA (US); James E. Clayton, San Jose, CA (US); David T. Nisius, Des Plaines, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 14/081,814

(22) Filed: Nov. 15, 2013

(65) Prior Publication Data
US 2015/0139386 A1    May 21, 2015

(51) Int. Cl.
| | |
|---|---|
| *G01V 5/00* | (2006.01) |
| *G01N 23/06* | (2006.01) |
| *H01J 35/10* | (2006.01) |
| *G01N 23/02* | (2006.01) |

(52) U.S. Cl.
CPC .............. *G01V 5/0016* (2013.01); *G01N 23/06* (2013.01); *G01V 5/0041* (2013.01); *H01J 35/101* (2013.01); *G01N 23/02* (2013.01)

(58) Field of Classification Search
CPC . G01V 5/0016; G01V 5/0091; G01V 5/0041; H01J 35/101; H01J 35/14; G01N 23/04; G01N 23/06; G01N 23/02; G01N 23/203; G01T 1/1648; G01T 3/00; G02B 27/30

USPC .......... 378/57, 106, 108, 146, 150, 160, 205, 378/5, 53, 62, 90, 95; 250/492.1, 492.3, 250/493.1
See application file for complete search history.

(56) References Cited

U.S. PATENT DOCUMENTS

| | | |
|---|---|---|
| 4,382,208 A | 5/1983 | Meddaugh et al. |
| 4,400,650 A | 8/1983 | Giebeler, Jr. |

(Continued)

OTHER PUBLICATIONS

Langeveld, Willem G.J. et al., "Intensity Modulated Advanced X-Ray Source (IMAXS) for Homeland Security Applications", IEEE Transactions for Nuclear Science, vol. 56, No. 3, Jun. 2009.

(Continued)

*Primary Examiner* — David A Vanore
(74) *Attorney, Agent, or Firm* — Cozen O'Connor; Brandon N. Sklar (57) ABSTRACT

Methods and systems for scanning objects comprising scanning a portion of an object by a first radiation beam having a first value of a beam characteristic, such as the dose, and detecting the first radiation beam after interaction with the object by a first detector. It is determined whether to change the first value to a second value based, at least in part, on the detected first radiation beam. That portion of the object is then scanned by a second radiation beam having the first value or the second value based on the determination. The second radiation is detected after interacting with the object by a second detector. The second detector may have a second resolution greater than a first resolution of the first detector. The first and second radiation beams may be formed by first and second slots angled with respect to each other.

29 Claims, 8 Drawing Sheets

(56) References Cited

U.S. PATENT DOCUMENTS

| | | | |
|---|---|---|---|
| 4,430,568 A | | 2/1984 | Yoshida et al. |
| 4,599,740 A | * | 7/1986 | Cable .................. 378/57 |
| 5,052,035 A | * | 9/1991 | Krupnick .................. 378/163 |
| 5,638,420 A | | 6/1997 | Armistead |
| 5,692,028 A | | 11/1997 | Geus et al. |
| 5,917,880 A | | 6/1999 | Bjorkholm |
| 6,292,533 B1 | | 9/2001 | Swift et al. |
| 6,366,021 B1 | | 4/2002 | Meddaugh et al. |
| 6,453,007 B2 | * | 9/2002 | Adams et al. .................. 378/90 |
| 6,937,692 B2 | * | 8/2005 | Johnson et al. .................. 378/57 |
| 6,954,515 B2 | | 10/2005 | Bjorkholm et al. |
| 7,257,188 B2 | * | 8/2007 | Bjorkholm .................. 378/53 |
| 7,339,320 B1 | | 3/2008 | Meddaugh et al. |
| 7,397,891 B2 | | 7/2008 | Johnson et al. |
| 7,619,363 B2 | | 11/2009 | Whittum et al. |
| 7,649,981 B2 | * | 1/2010 | Seppi et al. .................. 378/158 |
| 7,991,117 B2 | * | 8/2011 | Chen et al. .................. 378/95 |
| 8,054,937 B2 | * | 11/2011 | Langeveld et al. .................. 378/57 |
| 8,183,801 B2 | | 5/2012 | Chen et al. |
| 8,198,587 B2 | | 6/2012 | Whittum et al. |
| 2008/0014643 A1 | * | 1/2008 | Bjorkholm .................. 436/57 |
| 2009/0304150 A1 | * | 12/2009 | Metzler et al. .................. 378/62 |
| 2010/0127169 A1 | * | 5/2010 | Whittum et al. .................. 250/306 |
| 2010/0303206 A1 | * | 12/2010 | O'Dwyer et al. .................. 378/83 |
| 2012/0025084 A1 | * | 2/2012 | Virshup et al. .................. 250/361 R |
| 2012/0076257 A1 | * | 3/2012 | Star-Lack et al. .................. 378/4 |
| 2013/0170611 A1 | * | 7/2013 | Beckmann et al. .................. 378/9 |
| 2014/0270034 A1 | * | 9/2014 | Clayton et al. .................. 376/154 |
| 2014/0294147 A1 | * | 10/2014 | Chen et al. .................. 378/57 |

OTHER PUBLICATIONS

Langeveld, Willem G.J. et al., "Implementation of Noise Spectroscopy Using Biased Large-Area Photodiodes", IEEE Transactions on Nuclear Science, vol. 60, No. 2, Apr. 2013.

SILAC®, Datasheet, Siemens Industrial Linear Accelerator, Apr. 2012, Siemens AG.

* cited by examiner

FEEDBACK MODULATED RADIATION SCANNING SYSTEMS AND METHODS FOR REDUCED RADIOLOGICAL FOOTPRINT

FIELD OF THE INVENTION

Radiation scanning of objects, including large objects such as cargo containers, to identify contraband, with radiation dose modulation.

BACKGROUND OF THE INVENTION

Radiation is commonly used in the non-invasive inspection of objects, such as luggage, bags, briefcases and the like, to identify hidden contraband at airports and public buildings. Larger objects, such as cargo containers, are also inspected by radiation scanning. The contraband may include hidden guns, knives, explosive devices and illegal drugs, for example. One common inspection system is a line scanner, where the object to be inspected is passed between a stationary source of radiation, such as X-ray radiation, and a stationary detector. The radiation may be collimated into a fan beam, for example, for line (transmission) scanning. Radiation transmitted through the object is attenuated to varying degrees by material between the radiation source and the detectors. The attenuation of the radiation is a function of the density of the materials through which the radiation beam passes. The attenuated radiation is detected and radiographic images of the contents of the object are generated for inspection. The images show the shape, size, and varying densities of the contents.

The inspection of cargo containers at national borders, seaports, and airports, for example, is a critical problem in national security and trade enforcement. Due to the high rate of arrival of such containers, inspection requires rapid imaging of each container. Standard cargo containers are typically 20-50 feet long (6.1-15.2 meters), 8 feet high (2.4 meters), and 6-9 feet wide (1.8-2.7 meters). Larger air cargo containers, which are used to contain a plurality of pieces of luggage or other cargo to be stored in the body of an airplane, may be up to about 238×96×96 inches (6.0×2.4×2.4 meters), for example. Large collections of objects, such as many pieces of luggage, may also be supported on a pallet. Pallets, which may have supporting side walls, may be of comparable sizes as cargo containers and use of the term cargo container will generally encompass pallets, as well. MeV radiation sources are typically required to generate radiation with sufficient energy to penetrate through standard "cargo containers" and the larger air cargo containers.

It has also been proposed to scan large containers with mobile X-ray imaging systems. For example, U.S. Pat. No. 5,638,420 to Armistead discloses a mobile straddle inspection system, wherein a radiation source generating radiation in the MeV range is routed to one side of the frame and a detector array is mounted on an opposing side of the frame as the radiation source. The frame, which may be self-propelled, moves horizontally across the length of the container during scanning. Radiographic images are generated for analysis by an operator.

U.S. Pat. No. 5,692,028 to Geus et al. discloses an X-ray source mounted on a mobile vehicle and a detector supported by a portal shaped assembly extending from the vehicle. During inspection of an object, which can be another vehicle, the mobile vehicle is driven past the object, such that the object passes through the portal shaped assembly.

U.S. Pat. No. 6,292,533 B1 to Swift, et al. discloses a mobile X-ray inspection system for large objects, such as a cargo container carried by a vehicle, that uses an X-ray generating radiation source with a maximum radiation output of 450 keV. The source is supported on a truck and a pencil beam is generated to vertically scan the vehicle. Detectors, also supported on the truck or a boom extending from the truck, are provided to detect radiation transmitted through and scattered by the contents of the object. In use, a vehicle to be inspected parks alongside the scanning unit on the truck. The source and detectors are moved horizontally by a translation system within the truck to horizontally scan the vehicle.

Fixed inspection systems have also been proposed for inspecting large containers. For example, U.S. Pat. No. 4,430,568 to Yoshida discloses an X-ray system for the inspection of packages, including large shipping containers. A conveyor moves the package or container horizontally between the X-ray source supported on a floor and a detector array.

Similarly, U.S. Pat. No. 4,599,740 to Cable discloses a fixed inspection system, where an X-ray source transmits a continuous beam of radiation across a conveyor along which the containers to be inspected are moved. The container may be moved either continuously or incrementally. The radiation transmitted through a container is detected by a "folded" sensor screen or device having two, perpendicular arms, one extending vertically along a side of the container and the other extending horizontally over the top of a container during inspection. The folded sensor enables the system to have a smaller height than would otherwise be necessary in order to detect radiation transmitted through the entire container.

U.S. Pat. No. 5,917,880 to Bjorkholm discloses an X-ray inspection apparatus that may be used to inspect cargo containers with X-ray radiation of about 8 MeV, collimated into a vertical fan beam to scan a truck carrying the cargo. A first detector array is aligned with the fan beam to detect radiation transmitted through the truck. A second detector array is provided to detect radiation forward scattered through the truck. The truck is moved through the vertical fan beam. Data from both detectors is used to determine the average atomic number of the attenuating material in the truck to identify the material content in the truck. Images indicative of the material content are then prepared. Data provided by the first detector array is also used to form radiographs of the truck.

U.S. Pat. Nos. 6,937,692 and 7,397,891, which are assigned to the assignee of the present invention and are incorporated by reference herein, mount an x-ray radiation source and a radiation detector to rails on respective vehicles. The vehicles may be trailers and the rails may be expandable. A car or truck to be inspected, for example, is positioned between the vehicles and the carriages are moved along the rail to scan the car or truck.

High energy radiation scanning systems for scanning large objects, such as cargo containers, generate high energy in the MeV range, over a broad area. Exposure of the cargo containers and the environment to high doses of radiation could pose a threat to workers and other people in proximity to the radiation scanning system as well as to stowaways in the cargo containers, if present. Large amounts of shielding may be required to prevent leakage or scatter radiation to the environment, adding to the expense and size of the system. Radiation exposure in the environment is a threat in lower energy radiation scanning systems, as well. It could also pose a threat to drivers of vehicles being inspected.

In U.S. Pat. No. 7,991,117 B2, which is assigned to the assignee of the present invention and is incorporated by reference herein, the intensity of a radiation beam is modulated during scanning of an object based on the contents of the object to reduce radiation intensity when it is not needed. The information about the contents of the object may be based on historical records about the object or from the current scanning procedure. The information about the intensity modulation may take place essentially in real time.

SUMMARY OF THE INVENTION

In one example of an embodiment of the invention, radiation detected by a first detector from a first scan of a portion of an object provides feedback to the system to determine whether that portion needs to be subsequently scanned with a high or low dose radiation beam for satisfactory imaging and/or material discrimination. For example, if the radiation detected by the first detector after transmission through a first portion of the object is highly attenuated, then when that first portion of the object is scanned by the second radiation beam, a high dose of radiation is needed for satisfactory imaging and/or material discrimination. If the radiation detected by the first detector after transmission through a second portion of the object has low attenuation, in contrast, then when that second portion of the object is scanned by the second radiation beam, a lower dose of radiation would be sufficient for satisfactory imaging and/or material discrimination. By only using high doses of radiation when needed, radiation exposure to the environment is decreased. Other techniques for lowering radiation exposure to the environment are disclosed, as well.

In accordance with an embodiment of the invention, a method of examining an object is disclosed comprising scanning a portion of an object by a first radiation beam having a first value of a beam characteristic and detecting the first radiation beam after interaction with the object at a first location by a first detector having a first resolution. The method further comprises determining whether to change the first value of the beam characteristic to a second value different from the first value based, at least in part, on the first radiation beam detected by the first detector and scanning the portion of the object by a second radiation beam having the first value or the second value of the beam characteristic based, at least in part, on the determination. The second radiation is detected after interacting with the object by a second detector having a second resolution greater than the first resolution.

In this and other embodiments, the object may be moved with respect to the radiation source and the first and second detectors or the radiation source may be moved with respect to the object.

In addition, in this and other embodiments, the beam characteristic may comprise a dose of the radiation beam and the value of the dose may be changed by changing an energy, pulse repetition frequency, and/or the pulse width of the radiation beam, and/or changing a value of a current of a charged particle beam injected into an accelerator to generate the radiation beam. The portion of the object may be scanned by a second radiation beam having a high dose if the detected first radiation beam has high attenuation and the portion of the object may be scanned by a second radiation beam having a low dose if the radiation detected by the first detector has low attenuation.

In accordance with another embodiment of the invention, a method of scanning an object is disclosed comprising generating a radiation beam, collimating the generated radiation beam to form a first radiation beam, scanning a first portion of the object by the first radiation beam having a first value of a beam characteristic, and detecting the first radiation beam after interaction with the object. The method further comprises determining whether to change the first value to a second value different from the first value, based, at least in part, on the detected first radiation beam. The generated radiation beam is collimated to form a second radiation beam at an angle with respect to the first radiation beam. The first portion of the object is scanned by the second radiation beam having the first value or the second value of the characteristic, and the second radiation beam is detected after interacting with the object.

The first radiation beam may be formed in this and other embodiments by collimating the generated radiation beam by a first collimator defining a first slot to define the first radiation beam and the second radiation beam may be formed by collimating the generated radiation beam by a second collimator defining a second slot to define the second radiation beam. The first slot is angled with respect to the second slot and the first radiation beam is angled with respect to the second radiation beam. The first slot may extend only partially through the first collimator, to attenuate the first radiation beam.

The height of the contents of the object may be determined in this and other embodiments based on the detected first radiation beam and the generated radiation beam may be collimated to define a height of a portion of the generated radiation beam prior to collimating the generated radiation beam. The height of the second radiation beam may be defined based, at least in part, on the determined height. Reducing the height of the second radiation beam so that empty portions of the object are not irradiated further reduces the radiation footprint of the system.

In accordance with another embodiment of the invention, a radiation scanning system to examine objects comprises a radiation source configured to generate radiation beams having at least a first value of at least one beam characteristic or a second value of the at least one beam characteristic different from the first value. A first detector having a first resolution is positioned at a first location to detect the first radiation beam after interacting with a portion of the object. A second detector having a second resolution greater than the first resolution is positioned at a second location downstream of the first location to detect the second radiation beam after interacting with the object. A controller is configured to determine whether to change at least the first value of the beam characteristic to the second value based, at least in part, on the first radiation beam detected by the first detector, when the portion is scanned by the second radiation beam.

In accordance with another embodiment of the invention, a radiation scanning system to examine objects is disclosed comprising a radiation source configured to generate radiation beams having at least a first value of at least one first beam characteristic and a second value of the at least one beam characteristic different from the first value. A first collimator defines a first slot extending at least partially through the collimator to define a first radiation beam. A second collimator defines a second slot to define a second radiation beam. The first slot and the second slot are angled with respect to each other so that a portion of the object is scanned by the first radiation beam before being scanned by the second radiation beam. A first detector is positioned at a first location to detect the first radiation beam after interacting with the object and a second detector is positioned at a second location downstream of the first location to detect the second radiation beam after interacting with the object. A controller is configured to determine whether to change of least the first value of the beam characteristics to the second value based, at least in part, on the first radiation beam detected by the first detector value of the beam characteristics when the portion is being scanned by the second radiation.

A third collimator may be provided in this and other embodiments to define a height of at least the second radiation beam. The second collimator may be between the radiation source and the at least one first collimator or the second collimator may be between the at least one first collimator and the object. The first detector may comprise a plurality of detector arrays in at least partially different vertical locations. At least some of the plurality of detector arrays provide a separate output, which may be used to determine an approximate height of the contents in the object.

BRIEF DESCRIPTION OF THE DRAWINGS

FIG. 6b is a front view of the exit side of the first collimator of FIG. 6a;

DETAILED DESCRIPTION OF PREFERRED EMBODIMENTS

Radiation scanning systems and methods are described with reduced radiological footprint as compared to known radiation scanning systems. The reduced radiological footprint is provided by reducing unneeded radiation dose levels and/or limiting radiation exposure to only those locations of an object where it is necessary for satisfactory imaging quality and/or material discrimination. Since the radiation dose is reduced when higher doses are not necessary, image quality is not sacrificed. In addition heavy collimation is not needed. Radiation scanning systems with reduced radiological footprints may be more readily used in more diversely populated areas by reducing the risk of exposure to the public. They also provide lower doses to stowaways and drivers of vehicles being scanned, if either are present during scanning. The radiation scanning systems in accordance with embodiments of the invention may be mounted to the mobile and fixed inspection systems, such as those discussed above. Radiation dose may be varied by varying the energy, the pulse repetition frequency ("PRF"), the pulse width, and/or the current of the charged particle beam, such as the electron beam, injected into the accelerator of the radiation scanning system, for example. As is known in the art, radiation dose varies with the square of the energy, and linearly with each of the PRF, pulse width, and the charged particle current.

Figure 1:
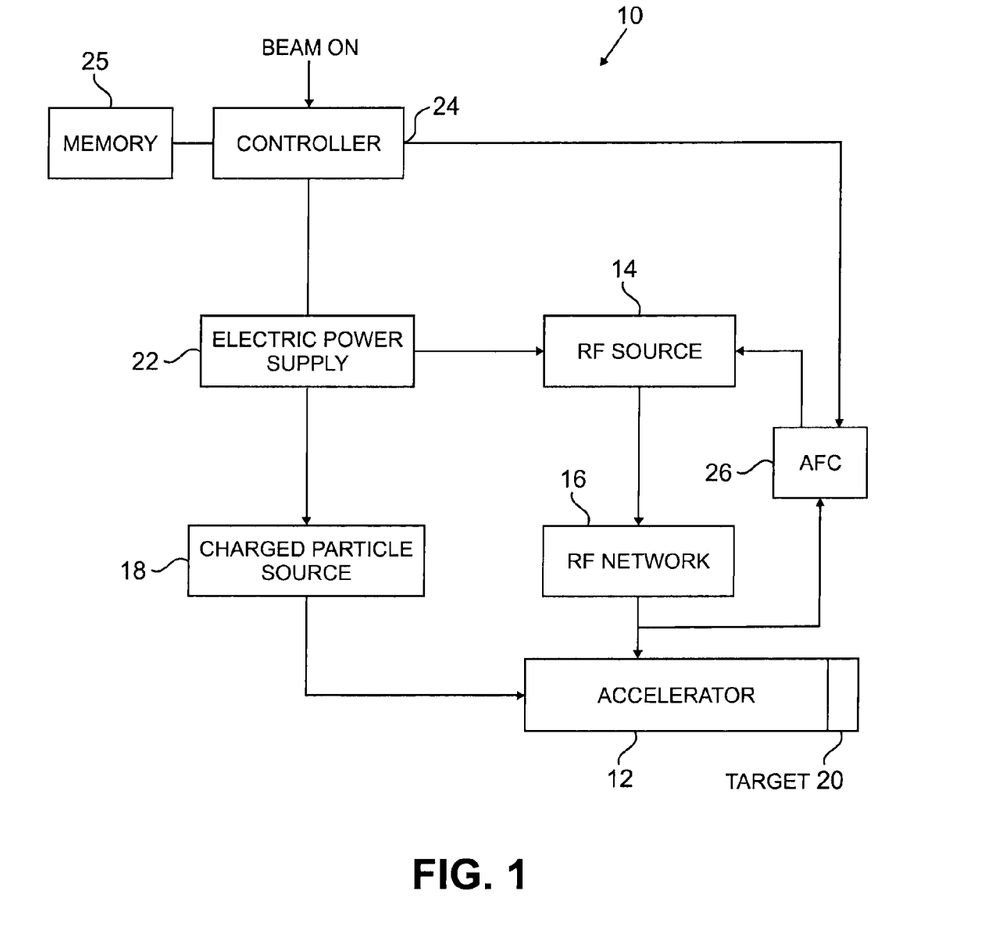
FIG. 1 is a block diagram of major components of an example of radiation source 10 configured to generate radiation, that may be used in embodiments of the invention.

FIG. 1 is a block diagram of major components of an example of radiation source 10 configured to generate radiation, that may be used in embodiment of the invention. The system 10 comprises an RF accelerator, such as a linear accelerator 12. An RF source 14, which may be a magnetron or a klystron, provides RF power to accelerator 12, through an RF network 16. The RF network 16 ensures that the RF source 14 is properly coupled with the accelerator 12 and isolates the RF source from reflected RF power and the frequency pulling effect caused by the accelerator. The RF network typically includes a circulator and an RF load (not shown) of the accelerator 12, for acceleration. A target 20, such as tungsten or another high atomic number material, is positioned for impact by the accelerated charged particles, to generate radiation by the Bremsstrahlung effect, as is known in the art. To generate X-ray radiation, the charged particle source may including a diode or triode type electron gun, for example.

An electric power supply 22 provides electric power to the RF source 14 and the charged particle source 18. The electric power supply is controlled by a controller 24, such as a programmable logic controller, a microprocessor, or a computer, for example. A memory device 25 is within or associated with the controller 25. An automatic frequency controller ("AFC") 26 is provided to match the resonance frequency of the accelerator 12 with the frequency of the RF source 14.

When a beam-on command is provided to the controller 24 by an operator, for example, the controller 24 turns on the electric power supply 22 to provide electric power to the RF source 14 and to the charged particle source 18. The electric power may be provided in the form of pulses of a few microseconds each, at a rate of up to a few hundred pulses per second, for example. The RF source 14 generates standing or travelling electromagnetic waves in the resonant cavities of the accelerator, which bunch and accelerate charged particles injected by the charged particle source 18. In this example, accelerated charged particles are directed toward the target 20. Impact of the accelerated charged particles on the target 20 causes generation of radiation by the Bremsstrahlung effect, as mentioned above, at a corresponding radiation pulse length and rate. The electric power supply 22 is turned off when radiation is no longer desired. Modifications to the radiation source 10 for use in the embodiments of the present invention are discussed below.

Figure 2:
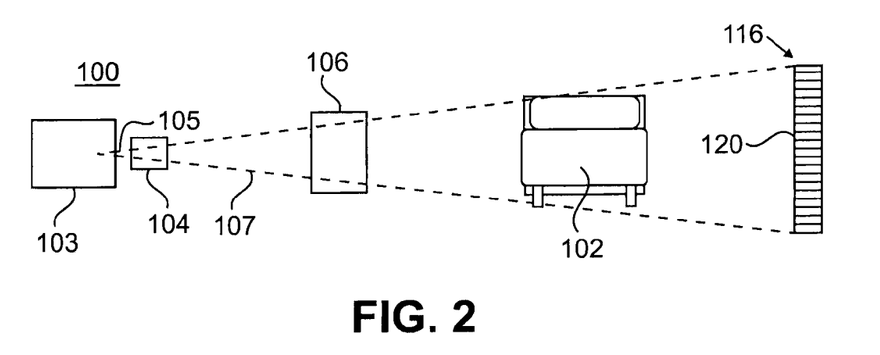
FIG. 2 is a side schematic front view of an example of a radiation scanning system in accordance with an embodiment of the invention.
Figure 3:
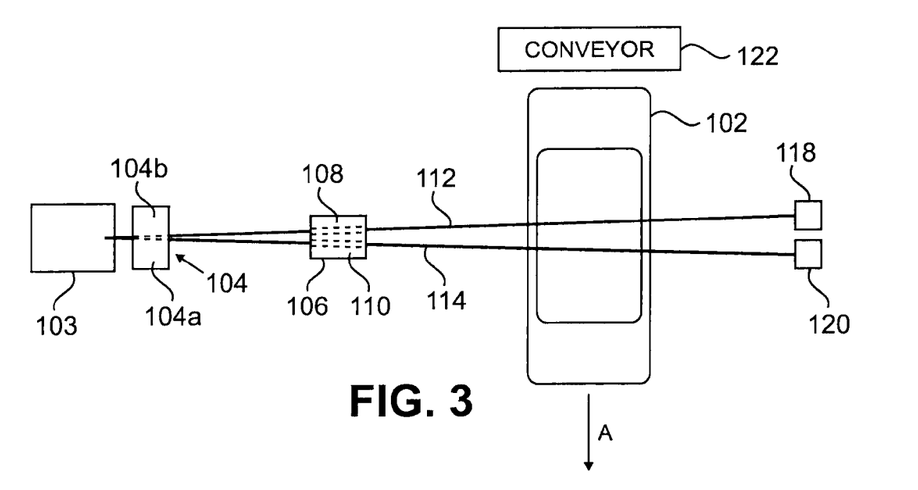
FIG. 3 is top view of the radiation scanning system of FIG. 2, showing the same components as in FIG. 2.
Figure 4:
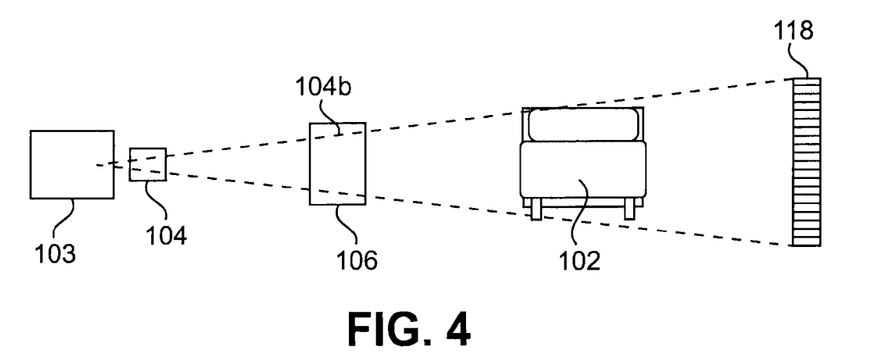
FIG. 4 is a side schematic rear view of the radiation scanning system of FIG. 2, showing a first upstream detector array.

FIG. 2 is a side schematic front view of an example of a radiation scanning system 100 in accordance with an embodiment of the invention. FIG. 3 is top view of the radiation scanning system 100 of FIG. 2, showing the same components as in FIG. 2 and a direction of movement A of an object 102 through the system. FIG. 4 is a side schematic rear view of the radiation scanning system 100 of FIG. 2. In the front view of FIG. 2 the direction of movement A is out of the page and in rear view of FIG. 4, the direction of movement is into the page. In the example of FIG. 2, an object 102, such as a car, is being scanned.

The system 100 comprises a radiation source 104, which may be similar to the radiation source of 10 of FIG. 1 or may be another type of radiation source, examples of which are described below. The radiation source 100 generates a first radiation beam 105. A first collimator 104 and a second collimator 106 are shown between the object 102 and the radiation source 100. The first collimator 104 collimates the generated radiation beam 102 to form a first collimated radiation beam 107 having a defined height, width, and shape. The first collimated radiation beam may be a fan beam, for example.

The second collimator 106 comprises first and second slots 108, 110, shown in phantom in the top view of phantom in FIG. 3, which simultaneously collimate the first collimated radiation beam 107 to form first and second scanning radiation beams 112, 114, respectively, as shown in the top view of FIG. 3. The collimators 104, 106 are discussed in more detail below. A detector 116 is shown receiving the radiation beam after transmission through the object 102.

In the top view of FIG. 3, the object 102 is moved in the direction of the arrow A by a conveyor indicated schematically by block 122. The conveyor 122 may comprise a moving conveyor, a moving track, moving belts, and/or moving chains, for example, as is known in the art. In this example, the detector 116 comprises first and second detectors 118, 120. The detectors 118, 120 may each be detector arrays. In FIG. 3, the first detector 118 is an upstream detector array and the second detector is a downstream detector array in relation to the movement of the object 102 in the direction of arrow A. The first upstream detector array 118 is positioned to detect the first scanning radiation beam 112 and the downstream detector array is positioned to detect the second scanning radiation beam 114, after each beam is transmitted through the object 102. In accordance with this embodiment of the invention, one portion of the object 102 is scanned by the first radiation beam 112 while a different portion of the object is scanned by the second radiation beam 114. The side schematic rear view of the radiation scanning system 100 of FIG. 2 shows the first, upstream detector 118. The downstream detector array 118 and the upstream detector array 120 may be separate or may be portions of a single detector array.

Figure 5:
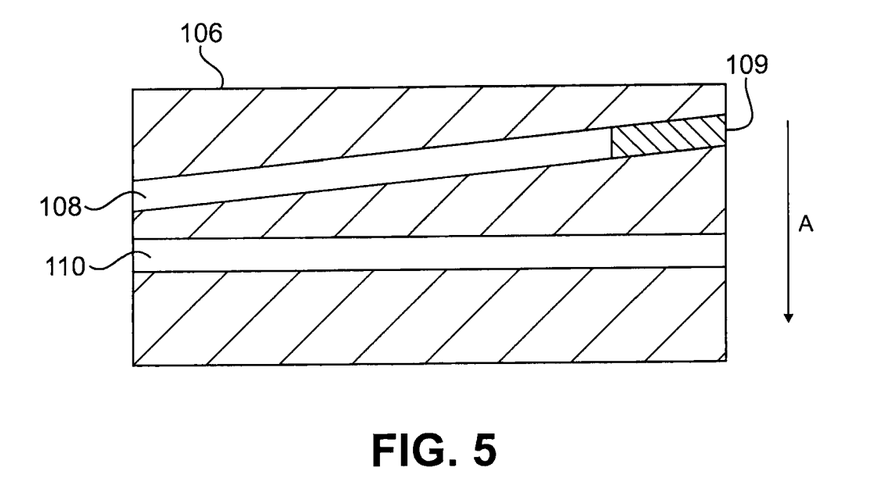
FIG. 5 is an enlarged, top cross-sectional view of the second collimator of FIG. 2, showing first and second slots for defining a first, preview radiation beam and second, primary radiation beam.

FIG. 5 is an enlarged, cross-sectional view of the second collimator 106 showing the first and second slots 108, 110. In this example the second slot 110 is perpendicular to the direction of movement A of FIG. 3. The first slot 108 is angled with respect to the second slot 110, so that the first scanning radiation beam 112 scans the object 102 before the second scanning radiation beam 114. The first slot 108 and the upstream detector array 118 are positioned so that the first radiation beam 112 is detected by the upstream detector after transmission through the object 102. The second slot 110 and the downstream detector array 120 are similarly positioned so that the second radiation beam 114 is detected by the downstream detector array 120 after transmission through the object 102. The radiation detected by the first detector 118 is used to determine whether respective portions of an object 102 under examination causes high or low attenuation, which information is used to determine characteristics of the second radiation beam 114. The first scanning radiation beam 112 is therefore referred to herein as a "preview radiation beam" 112 and the first detector 118 is referred to as a preview detector 118. The second radiation beam 114 is referred to herein as a "primary beam radiation" 114. In accordance with this embodiment of the invention, the preview radiation beam 112 and the primary radiation beam 114 are simultaneously generated and simultaneously scan different portions of the object 102, although this is not required.

If the radiation detected by the first, preview detector 118 after transmission through a first portion of the object 102 is highly attenuated, then when that first portion of the object is scanned by the second, primary radiation beam 114, a high dose of radiation will be needed for satisfactory imaging and/or material discrimination. If the radiation detected by the first detector 118 after transmission through a second portion of the object 102 has low attenuation, in contrast, then when that second portion of the object is scanned by the primary radiation beam 114, a high dose of radiation is needed for satisfactory imaging and/or material discrimination. By providing high doses of radiation by the primary radiation beam 114 only when necessary for satisfactory imaging and/or material discrimination and providing lower doses of radiation by the primary radiation beam when higher doses are not needed, radiation exposure to the environment is reduced.

The output of the preview detector 118 may be used to generate an attenuation map of the object 102, which shows the attenuation values of respective portions of the object 102. The attenuation values may be compared to one or more thresholds and/or ranges to determine whether the attenuation is high (the attenuation is greater than the threshold), or the attenuation is low (the attenuation is less than the threshold), or to determine degrees of high and low attenuation. If degrees of high and low attenuation are determined, then the primary radiation beam 114 may have multiple degrees of high and low doses, as well. For example, the radiation source 104 may be configured to generate primary radiation beams 114 having a high dose, a moderately high dose, a moderately low dose and a low dose, based on the results of scanning by the preview radiation beam 112, by varying different characteristics of the primary radiation beam. Multiple thresholds and/or ranges may be provided when there are multiple dose options. Thresholds and ranges may be determined for a particular system based on testing conducted by the system during a calibration procedure, as well as on the desired imaging quality and/or material discrimination sensitivity and specificity. Radiation beam generation at of desired dose levels is discussed further below.

Since the preview radiation beam 112 is only used to characterize the attenuation of respective portions of the object, the preview radiation beam 112 does not need to have as high a dose as the primary radiation beam 114, which is used for imaging and/or material discrimination. The dose of the preview beam 112 may be reduced with respect to the primary radiation beam 114 in one by providing a first slot 108 that does not extend completely through the second collimator 106. Collimator material or another material 109 may be located in the distal end of the first slot 108 to attenuate the preview radiation beam 112, for example. The length of the material 109 is determined to provide the desired attenuation, in manners known in the art. Alternatively or in addition, the slot 108 may be narrower than the slot 110. Lowering the dose of the preview radiation beam 112 further lowers the radiation exposure to the environment by the radiation system 100.

While in the example of FIGS. 2-4, first and second slots 108, 110 are configured so that the primary radiation beam 114 is perpendicular to the direction of motion of the object 102 and the preview radiation beam 112 is not perpendicular to the direction of motion, the slots may be configured to define the primary beam 114 and the preview beam 112 at other angles, as well. For example, the preview radiation beam 112 may be perpendicular to the direction of movement A, or neither beam may be perpendicular to the direction of movement.

Figure 6A:
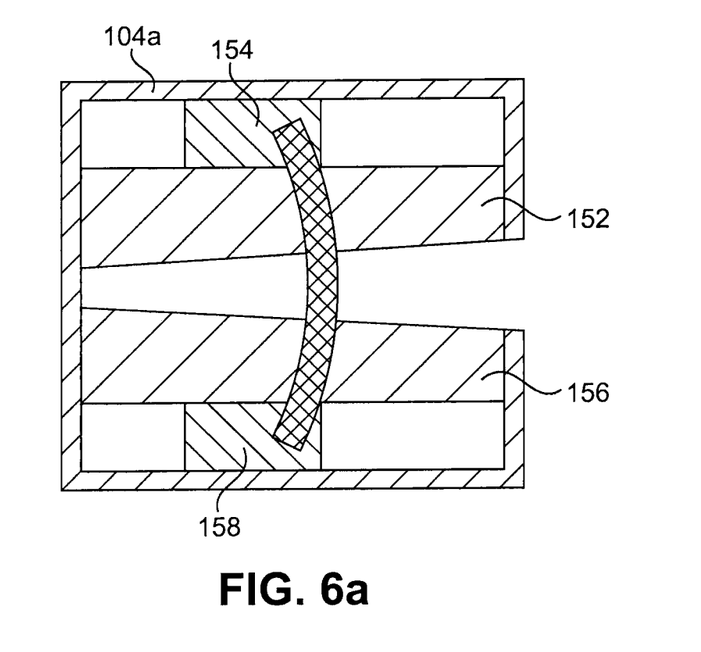
FIG. 6a is an enlarged, side cross-sectional view of the first collimator of FIG. 2, which defines a height of the primary and preview radiation beams.

FIG. 6a is a side, cross-sectional view of the first collimator 104 in the front view of FIG. 2, which defines a height of the primary radiation beam 114. In this example, the first collimator 104 comprises a variable collimator aperture A in the downstream section 104a of the collimator to define a height and width of the primary radiation beam 114, and a fixed collimator B in the upstream section 104b to define a height and width of the preview radiation beam 112, as indicated in FIG. 3.

Figure 6B:
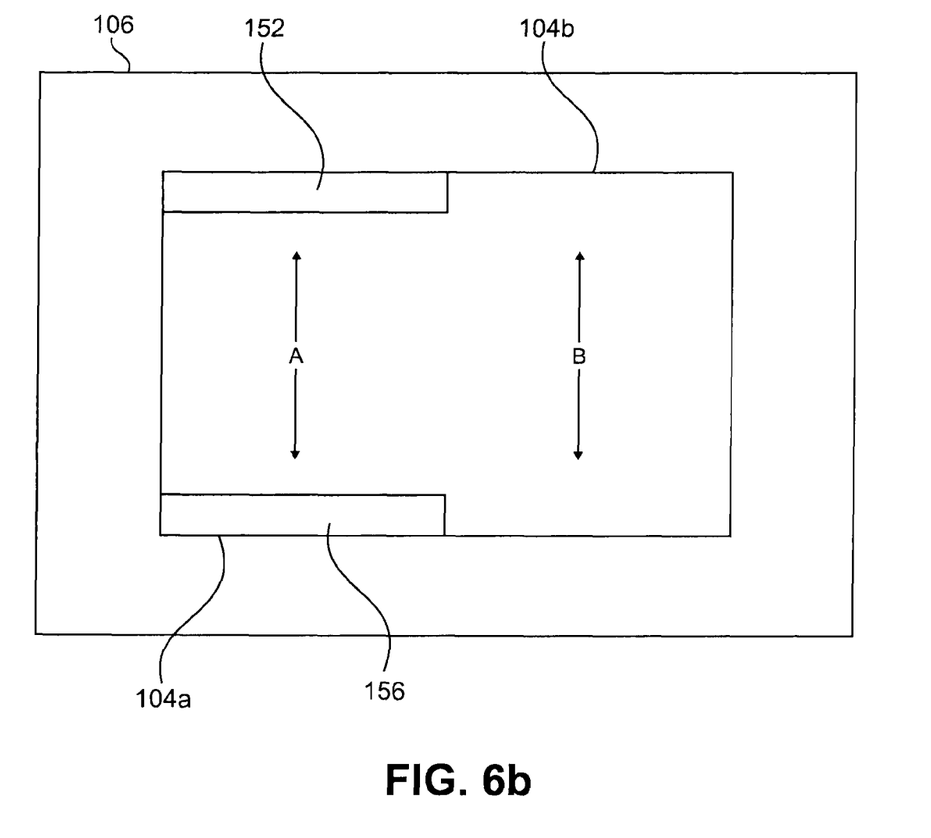

FIG. 6b is a front view of the exit side 104c of the first collimator 104, showing the downstream section 104a, including the variable collimator aperture A, and the upstream section 104b including the fixed collimator B. The primary radiation beam 114 and the preview radiation beam 112 may both be fan beams, although the primary radiation beam may have a different height than the preview radiation beam. Both the preview and primary beams 112, 114 may also have other shapes, such as a cone beam, for example. The preview and primary beams 112, 114 may also have different shapes from each other. For example, the preview radiation beam 112 may be a fan beam and the primary radiation beam may be a cone beam, or vice-a-versa, for example.

As shown in FIG. 6a, the variable collimator aperture 104a comprises a top jaw 152 controlled by a top jaw actuator block 154 and a bottom jaw 156 controlled by a bottom actuator block 158. The top and bottom jaws 152, 156, which may be separately controlled by the controller 24 or other such processing device, are moved across a rail by the top and bottom actuator blocks 154, 158 respectively. Two blocks per jaw may be used, for example. Each block have a length of from about 44.6 mm to about 197.9 mm, for example. The top and bottom jaws 152, 156 are also shown in FIG. 6b in a position defining a primary radiation beam 114 with less vertical expanse than the preview beam 112.

The curved bearing rail may be a THK model RCR, available from THK Global, Schaumburg, Ill., for example. Two bearing rail arcs may be mounted concentric with the focal spot of the primary scanning beam, one for each jaw. Each bearing rail arc supports a respective jaw. A straight rail may be used, instead.

The variable operative collimator 104a defines the upper and lower boundaries of the primary radiation beam 114 by positioning the upper and lower jaws 152, 154. The vertical expanse of the primary radiation beam 114 may thereby be adjusted so that the vertical expanse of the beam is no wider (higher or lower) than necessary to scan the object 102. This can be particularly useful in scanning systems that examine objects of varying heights such as cars and trucks, luggage of varying heights, and/or cargo containers of varying heights, for example. In addition, an object 102, such as a cargo container or railroad car, may not be completely filled. Materials that need to be examined may be at a lower portion of the object 102 while the upper portion is air, which need not be scanned. In this way, the exposure of the environment to unnecessary radiation is limited, reducing risks to operators of the system, etc. The controller 24 or other such processing device may control the height of the radiation beam based, at least in part, on the radiation detected by the preview detector 118 as discussed further below.

Other types of actuating devices may also be used, such as hydraulic, pneumatic, electrical, or mechanical activators. U.S. Pat. No. 6,954,515 B2, which is assigned to the assignee of the present invention and is incorporated by reference herein, describes several techniques for electromagnetically generating multiple, narrower radiation beams to encompass an object, centered as different postings of the object, instead of a single wider radiation beam. These techniques may be used to scan a desired height of an object by the generation of a suitable number of radiation beams. While two collimators 104, 106 separated by a distance are shown in the Figures, the two collimators may be adjacent to each other, or may be parts of a single collimating device.

Other collimation systems may also be used. For example, a plurality of collimators of different heights and widths may be mounted on a rotating wheel. An appropriate collimator may be moved into position based on the radiation detected by the preview, upstream detector array, under the control of the processing device, for example.

Figure 7:
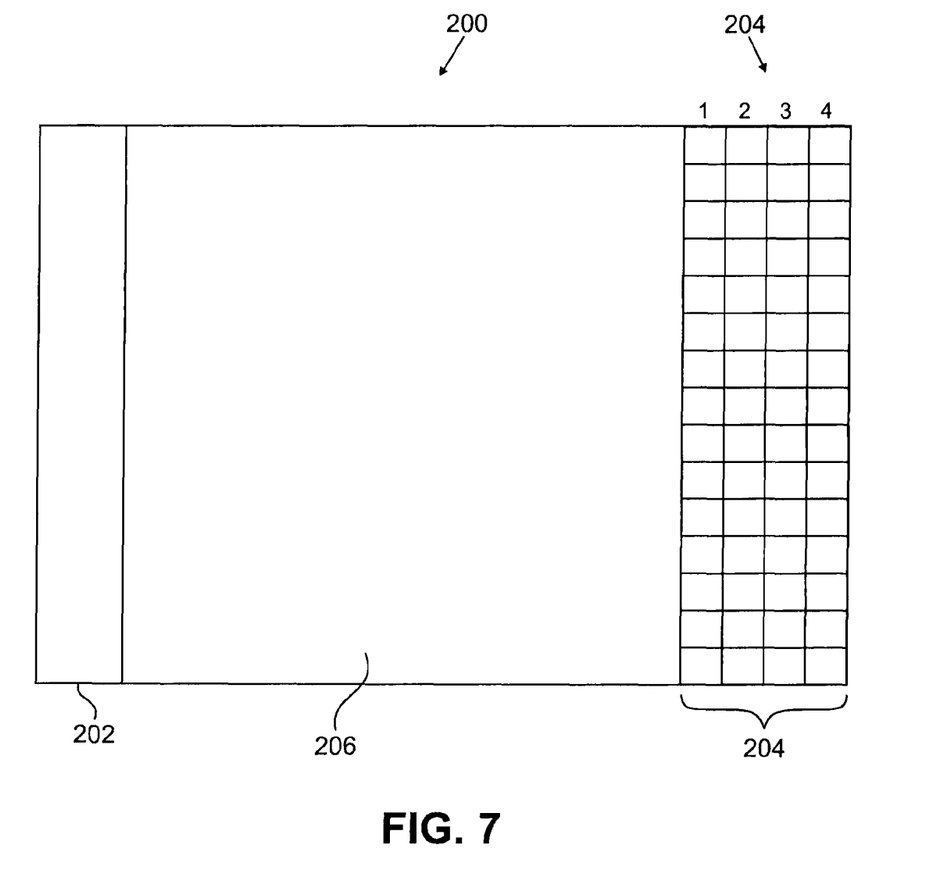
FIG. 7 is a front view of an example of a single detector array with a preview detector array portion and a primary detector array portion 204.

The preview detector 118 and the primary detector 120 may be separate detectors or detector arrays or may be part of the same detector array. FIG. 7 is an example of a single detector array 200 with a preview detector array portion 202 and a primary detector array portion 204. An intermediate portion 206 is provided between the preview detector portion and the primary detector portion, without detector elements, because they are not needed in that location.

In accordance with embodiments of the invention, the preview detector 118 or preview detector array 202, and the corresponding primary detector 120 or primary detector array portion 204 may have different configurations, respectively. In one example, the preview detector array portion 202 has a "sparse" configuration. The term "sparse" in this context means that the preview detector 118/detector array portion 202 has less resolution than the corresponding primary detector 120/detector array portion 204. Resolution may refer to energy discrimination or imaging resolution, for example. Since the preview detector 118/preview detector array portion 202 is used to provide a general characterization of the attenuation of the contents of a portion of an object 102 as high or low density, or air, as discussed further below, without determining the shapes or actual composition of the content, low resolution is acceptable. The use of low resolution where it is not needed also reduces costs.

Low resolution may be provided by having fewer, larger pixels in the preview detector 118/detector array portion 202 than in the primary detector/detector array portion 120, 204. In one example, it is sufficient to obtain an average attenuation over an entire vertical column or a few portions of the vertical column in the preview detector 118 preview detector array portion 202. Each vertical column may be continuous or discontinuous, with gaps provided between detector portions or modules, for example.

In scanning cargo containers, for example, the preview detector array 118/detector array portion 202 may have pixels of from about 3 cm×3 cm to about 25 cm×300 cm. In one example, the pixels may be 25 cm×5 cm. The primary detector 120/detector array portion 204 may have a conventional configuration including a plurality of detector elements providing a typical resolution and small pixels for similar applications. For example, the primary detector 118/detector array portion 204 may have pixels from about 10 mm×10 mm to about 400 microns×400 microns, for example. The pixels of the primary detector 118/detector array portion 204 may be less than 10 mm×10 mm or less than 5 mm×5 mm, for example. The pixels in the primary detector 118/detector array portion 204 may be 4.5 mm×4.5 mm, for example. In one example, the detector array 200 is 30 cm wide and 25 cm tall.

A sparse configuration may be provided by inexpensive, thin scintillators and screens providing low resolution, large pixel readout, for example. In one example, the preview detector 118 comprises a scintillator coupled to a photomultiplier tube ("PMT"). The scintillator may comprise appropriate scintillator materials such as polyvinyl toluene (PVT), for example. Undoped cesium iodide (CsI) may be used, instead, for example. In a current-integrating mode, PVT or thallium-doped CsI may be used. Cadmium tungstate ($CdWO_4$) may also be used, if desired. However, cadmium tungstate (CdWO$_4$) is expensive and is not needed in the primary detector 120 detector array portion 204.

The primary detector array portion 204 (or the separate detector 120) may comprise of a plurality of vertical column arrays of detector elements. Four columns 204-1, 204-2, 204-3, and 204-4 are shown in this example. More or fewer columns may be provided. The primary detector 120/detector array portion 204 may comprise undoped CsI or thallium doped CsI, or cadmium tungstate (CdWO$_4$), for example.

In one example, the data collected from each column for the same region is integrated by time delay integration and combined into a single image. This allows for faster imaging without compromising image quality. The size of the region detected by the preview detector array portion 202 and used to determine the dose applied to a region when scanned by the primary radiation beam 114 need not be the same size.

Figure 8A:
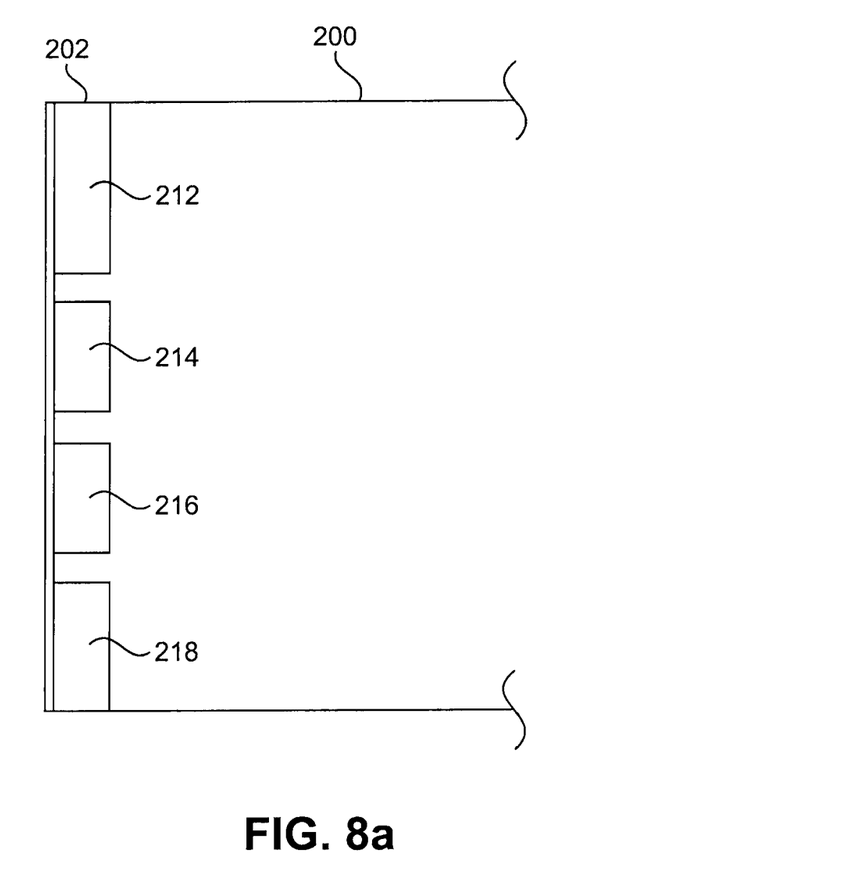
FIG. 8a is a front view of an example of a preview detector array configured to determine an approximate height of material to be scanned within an object, in accordance with an embodiment of the invention.

As discussed above, the first variable aperture collimator 104 is provided to limit the height of the primary radiation 114 beam to scan only the portion of the object 102 containing material. This further limits the amount of radiation delivered into the environment and the risks associated therewith. FIG. 8a is front view of an example of an arrangement of preview portions of detector arrays 200 that may be used to determine an approximate height of material to be scanned within the object 102 in accordance with an embodiment of the invention.

In the example of FIG. 8a, the detector arrays 200 are stacked to form four vertically arranged preview detector arrays 212, 214, 216, 218. If the height of the contents of the object 102 extends from the bottom to the top of the object 102, all the detector arrays 212-218 will show attenuation of the preview radiation beam 112 greater than a predetermined threshold, for example. If attenuation above a predetermined value of a portion of the object 102 is only indicated by detectors arrays 214-218, then the height of the material in that portion of the object 102 is no greater than the top of the detector array 214. The remainder of that portion of the object is air. Since the primary radiation beam 114 need not irradiate air, the upper boundary of the primary radiation beam 114 when scanning this portion of the object 102, may have a reduced height. Similarly, if attenuation above the predetermined value is only detected by detector arrays 216 and 218, then the primary radiation beam 114 need not irradiate the upper half of the object 102. If attenuation above the predetermined value is only detected by the lower detector array 218, then the primary radiation beam 114 need only irradiate the bottom quarter of the object 114. The upper boundary of the primary radiation beam 114 may then be suitably reduced by the upper activator jaw 152. If only one or both of the middle detector arrays 214, 216 detect greater than the predetermined threshold of attention, then the bottom boundary of the primary radiation beam 113 may be raised by the lower activator jaw 156.

In this example, the radiation dose of the preview radiation beam 112 may be further decreased by providing vertical slots in the collimator to define a separate preview beam for each detector array 212, 214, 216, 218, so that the spaces between the arrays are not irradiated.

Figure 8B:
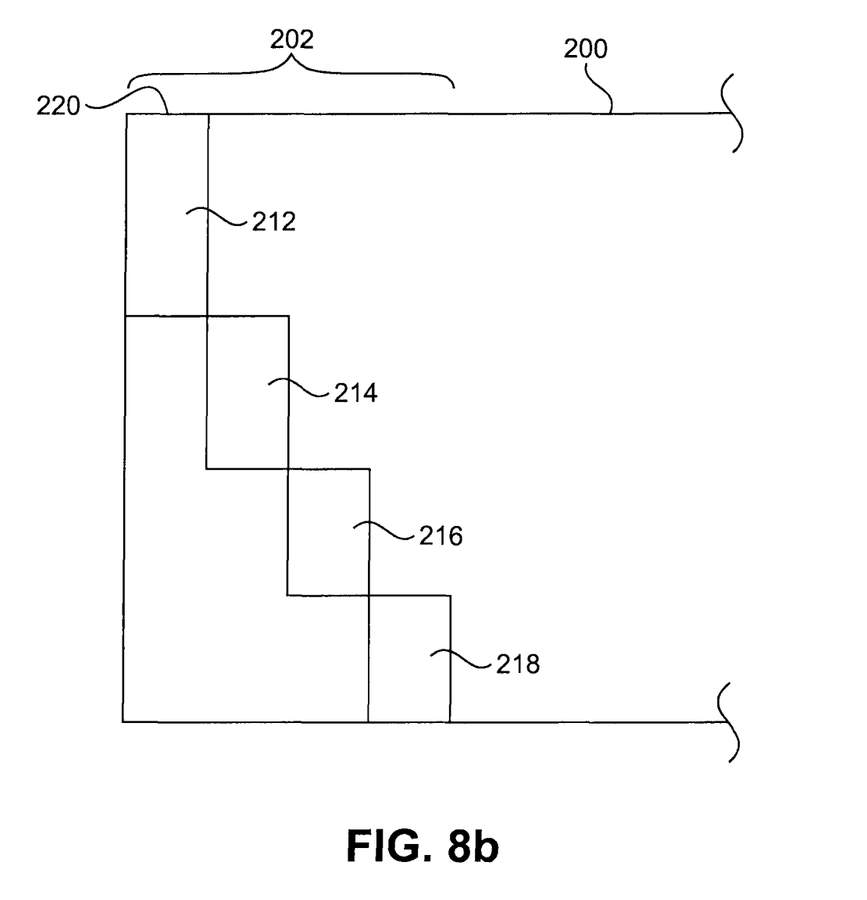
FIG. 8b is a front view of another example of a preview detector array configured to determine an approximate height of materials to be scanned within an object.

In another example, the plurality of vertically extending preview detector arrays may be staggered horizontally, as shown in FIG. 8b. In this example, the width of the preview beam 112 may be wide enough to encompass the width "W" of the all the columns 212-218 of the preview detector array 202. In another example, multiple staggered slots may be provided in the collimator 106 to form the preview beam 112, one for each of the staggered detector array 212-218.

It is believed that embodiments of the invention can decrease the radiation exposure to the environment by about 10 times by varying the dose of the primary radiation beam 114 based on the radiation detected by the preview detector 108 and by varying the height of the primary radiation beam may decrease overall radiation dose by about 10 times, for example.

The radiation scanning system 100 may be stationary and the object 102 to be examined may be moved with respect to the scanning system 100, between the radiation source 104 and the detectors 118, 120 or detector array 200, or the object may be stationary and the radiation scanning system 100 may be moved with respect to the object. In a system in which the radiation source 104 and detector/detectors 118, 120, 200 are stationary, the object may be moved by a conveyor 122, as discussed above with respect to FIG. 3.

In a system 100 where the object is stationary, the radiation source 100 and detector/detectors 118, 120, 200 are mounted to one or more movable arms, booms, frames or carriages that are moved across the object 102, for example, as discussed above. The radiation scanning system 100 may be incorporated in any of the prior art inspection systems discussed above or in other mobile and stationary systems, including commercially available systems. Commercially available systems are provided by Rapiscan Systems, Torrance, Calif.; Smith's Detection, Edgewood, Md.; American Science and Engineering, Billerica, Mass.; and Passport Systems, Inc., Billerica, Mass., for example.

The angle between the first and second slots 108, 110 may be determined based on the speed of movement between the scanning system 100 and the object 102, such as the speed the conveyor 122 moves the object through the preview and primary radiation beams 112, 114, or the speed the radiation scanning system 100 is moved across the object, as well as the distances between the radiation source 104 and the object, and the object and the preview and primary detectors/detector arrays. The angle may range from about 1 degree to about 30 degrees, for example. In an exemplary radiation scanning system 100, where the distance between the radiation source 104 and the detector array 200 is about 500 cm the distance between the rear face of the object and the detector array is 25 cm, the angle between the preview beam 112 and the primary beam 114 is 2.86 degrees, then the distance between the preview detector array portion 202 and the primary detector array portion 204 (in FIG. 7) may be about 25 cm, for example. When the object 102 is a standard cargo container having a height of 8 feet (2.4 meters) in such a system, multiple detector arrays 200 may be vertically stacked to form a detector array unit having a height of about 23 feet (701 cm), for example. The multiple detector arrays 200 may also be stacked and arranged in an arch.

If the accelerator 104 is operating at 300 Hz, for example, it can switch from pulse to pulse in about 3.3 milliseconds. This would allow for a maximum scanning speed of about 75 meters per second (0.25 m/0.00335) (270 Km/hour), which is much faster than known scanning systems. If the object 102 is stationary and the radiation scanning system is moved with respect to the object, comparable scanning speeds may be achieved.

As discussed above, the radiation source 104 is capable of changing the dose of the primary radiation beam 114 based on the results of scanning by the preview beam 112. For example, the radiation source 104 may be a switchable energy radiation source, as described in U.S. Pat. No. 7,619,363B2, U.S. Pat. No. 7,339,320 B1, U.S. Pat. No. 6,366,021, U.S. Pat. No. 4,400,650, and U.S. Pat. No. 4,382,208, for example, which are assigned to the assignee of the present invention and are incorporated by reference herein. In these cases, the radiation source 104 may be configured to be switchable between Bremsstrahlung spectrums having maximum energy outputs of 3 MeV and 5 MeV, 5 MeV and 9 MeV, or 6 MeV and 9 MeV, for example, under the control of the controller. As discussed above, the higher maximum energy outputs may be used when the primary radiation beam 114 is scanning portions of an object 102 that cause high attenuation, based on scanning of that portion of the object 102 by the by the preview radiation beam 112. When scanning by the preview beam indicates that a region contains low density material, then when that portion is scanned by the primary radiation beam 114, the energy of the primary radiation beam is switched to or maintained at a lower energy since the higher energy is not needed.

The radiation source 104 may also be an interlaced radiation accelerator, as described in U.S. Pat. Nos. 8,198,587 B2 and 8,183,801 B2, which are assigned to the assignee of the present invention and are incorporated by reference herein, for example. These patents disclose generating different electrical powers by a power generator in an interlaced manner to rapidly switch between the generating high and low energy radiation beams. Dose variation is also described in U.S. Pat. No. 8,183,801 by varying the voltage provided by an electric power supply 22 to a charged particle source 18, such as an electron gun. (See FIG. 1). The energies of the primary radiation beam 114 may thereby be varied depending on the radiation detected by the preview detector 113, as discussed above. In one example, the radiation source 114 may be configured to only generate radiation at a low energy, and then switch to interlaced operation for imaging and/or material discrimination when a highly attenuating portion of an object, if any, is being scanned by the priority beam 114. It is noted that if the primary radiation beam 114 is operating is an interlaced mode, so is the preview radiation beam 112. Similarly, when the primary radiation beam 114 is scanning at a high dose, so is the preview radiation beam. In addition or instead of varying the energy, the dose may be varied as described in U.S. Pat. No. 8,183,801 B2.

The radiation source 104 may also be an intensity modulated X-ray radiation source as described in U.S. Pat. No. 7,991,117 B2, which is assigned to the assignee of the present invention and is incorporated by reference herein, which discloses intensity modulation of an X-ray a radiation pulse by controlling the overlap of a current pulse from a charged particle source 18 and a radio frequency pulse from the RF source 14 provided to the accelerator 12. An attenuator may also be selectively positioned with respect to a radiation beam before the beam irradiates the object 102. The intensity of the primary radiation beam 114 may thereby be increased or decreased based on the radiation detected by the preview detector 112.

The radiation source may also be an intensity modulated X-ray source as described in U.S. Pat. No. 8,054,937 and Langeveld, et al., "Intensity Modulated Advanced X-Ray Source (IMAXS) for Homeland Security Application," IEEE Transactions for Nuclear Science, Vol. 56, No. 3, June 2009, for example, which are incorporated by reference herein. These references describe the modulation of pulse duration and/or beam current, enabling finer control of the radiation dose among multiple high and low dose levels. Energy modulation may also be provided.

A SILAC® Linear Accelerator System, available from Siemens AG, Germany, may also be used, which is said to allow for variation in electron energy, pulse width, repetition frequency, or beam current. This product also enables finer control of the radiation dose among multiple high and low dose levels.

Figure 9:
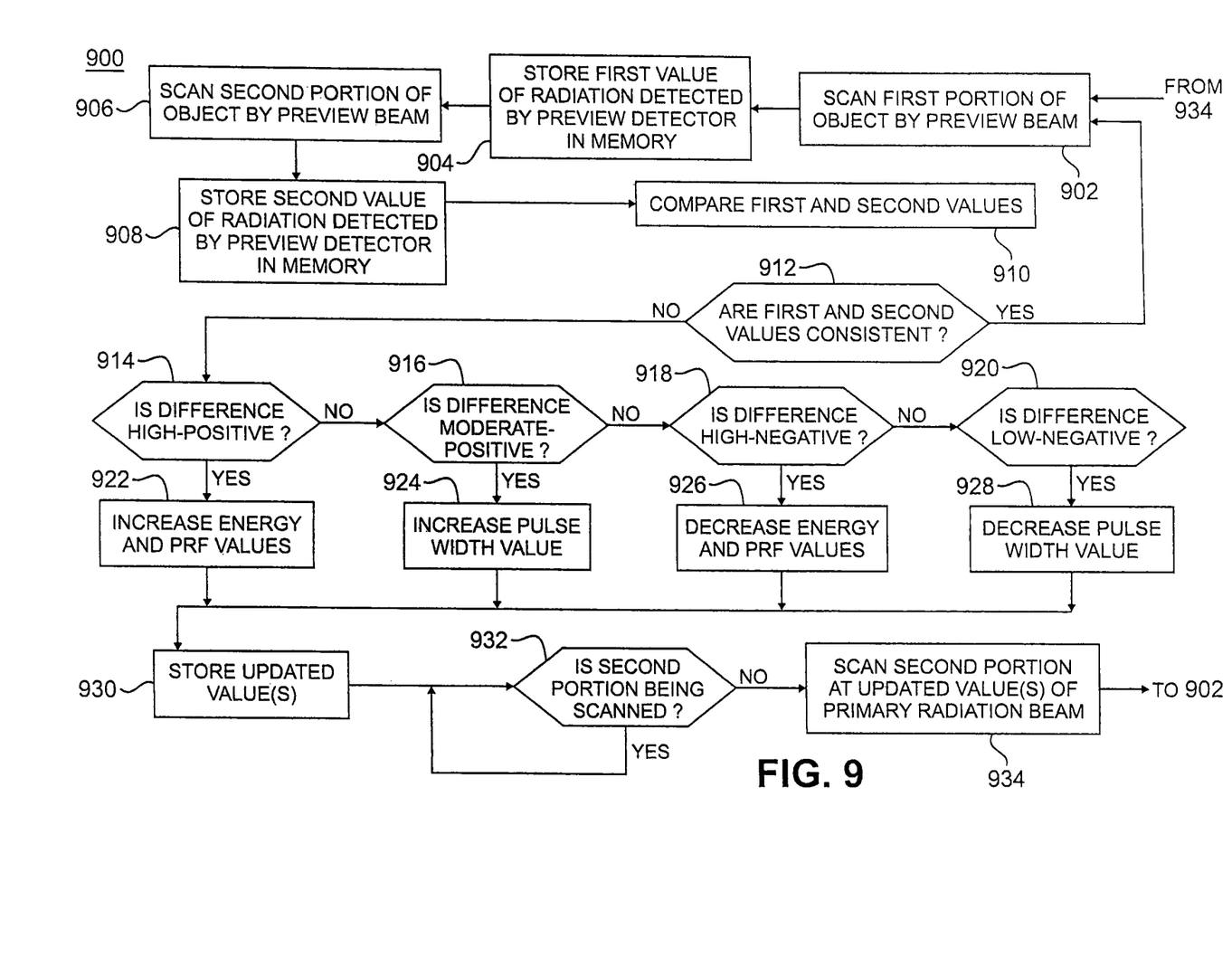
FIG. 9 is a flowchart of an example of a method of changing characteristics of the primary radiation beam based on the preview radiation beam, in accordance with an embodiment of the invention.

FIG. 9 is an example of a method 900 of dose adjustment of the primary radiation beam 114 based on the radiation detected by the preview detector 118, where the radiation source 104 is configured to change the dose of the primary radiation beam 120 by changing the energy, pulse repetition frequency ("PRF"), and/or pulse width of the generated radiation beam 105, as necessary. Such variation may be provided by the systems described in U.S. Pat. No. 8,054,937 and Langeveld, et al., "Intensity Modulated Advanced X-Ray Source (IMAXS) for Homeland Security Application," IEEE Transactions for Nuclear Science, Vol. 56, No. 3, June 2009, and the SILAC® Linear Acceleration System, described above, for example. In this example, the dose of the primary radiation beam 120 is adjusted by the controller 24 based on a difference between a current measurement by the preview detector 108 and the prior measurement of the preview detector, under the control of suitable software, for example. The primary radiation beam 114 may have four dose levels in this example.

A first portion of the object 102 is scanned by the preview beam 112 in Step 902 and the measurement of the preview detector 118 is stored in memory 25, in Step 904. The first measurement is based on the detection of a preview radiation beam 112 that in this example is in a low energy, such as 3 MeV, a minimum pulse width, and a minimum PRF, for example A second portion of the object is scanned by the preview radiation beam 118 in Step 906 and the measurement of the preview radiation beam after transmission through the second portion of the object is stored in the memory 25 by the controller 24, in Step 908. The outputs of the preview detector 118 are indicative of the attenuation of the preview radiation beam 112 due to the contents of the object in the portion X of the object 102 being scanned.

The controller 24 then compares the second output of the of the preview detector 118 during the second measurement to the first output of the preview detector 118 during the first measurement, in Step 910, and determines whether the second measurement is consistent with the first measurement, in Step 912. In this example, "consistent" means that the difference between the second measurement and the first measurement is within a predetermined, small range. The difference may be determined by subtracting the first output value, second output value, or by subtracting the second output value from the first output value. In this example, the second output value is subtracted from the first output value.

If the second output value is consistent with the first output value (Yes in Step 912), the primary radiation beam 114 will not be changed and the second portion of the object will be scanned at the same characteristics of the primary radiation beam 114 as the first portion when it passed through the primary radiation beam. The process then returns to Step 902 to evaluate a subsequent, new first portion of the object.

If the second output value is not consistent with the first output value in Step 912, then the method proceeds to Step 914, where the controller 24 determines the degree of the difference between the second and first output values. In this example, the controller 24 determines whether the difference between the first output and the second output is high and positive ("high-positive"), because the first output is much higher than the second output. This may be determined by the controller 24 by comparing the difference between the first and second output values to a first threshold or range stored in the memory 25. If the difference is greater than the threshold or outside of the range, then the difference is high-positive. A Yes determination in this example is indicative of a large decrease in detected radiation by the preview detector 118 in the second measurement caused by a large increase in the attenuation of the primary radiation beam 114, as compared to the prior scanned portion.

In response to a Yes determination in Step 914, the controller 24 in this example increases the value of the dose of the primary radiation beam 114 to be generated when the same region passes through the primary radiation beam 114, by increasing the energy of the radiation beam and the pulse repetition frequency ("PRF") of the primary beam in Step 922. Better imaging and/or material discrimination of the highly attenuating material in that portion of the object 102 may thereby be achieved.

As discussed above, dose is proportional to the square of the energy and is linearly proportional to the pulse repetition frequency of the primary radiation beam 114. Increasing the energy therefore provides the greatest increase in dose while the increase in the PRF provides an additional but smaller increase than the increase in energy. Alternatively, only an increase in energy may be provided in Step 922 and the need for an additional increment in dose to be provided by the increase in PRF may be determined in a separate comparison Step 922 by comparison to another threshold or range, for example. The updated value of the energy and the PRF are stored in the memory 930 in Step 930, for use when the second portion of the object is scanned by the primary radiation beam 114.

If the determination in Step 914 is not high-positive, the controller 24 determines whether the difference between the current measurement and the previous measurement is "moderate-positive," in Step 916. By "moderate-positive" is meant that the difference between the first output and the second, current output is positive (the first value of the first output is greater than the value of the second, current output), output greater than the small, predetermined range defining "consistent measurement, which was already determined in Step 912, and less than the value of the first threshold, for example. This is indicative of a moderate increase in the attenuation of the primary radiation beam 114 caused by the material in the current portion or range of the object being scanned.

In that case, the controller 24 increases the value of pulse width of the primary radiation beam 114 to be generated when that portion of the object is scanned by the primary beam 114, in Step 924, and stores the value in the memory 25, in Step 930. As discussed above, the dose varies linearly with the pulse width.

If the controller 24 determines that the difference is not moderate-positive, the controller proceeds to Step 918 to determine whether the difference between the first and second output values is high and negative ("high-negative") (the value of the second, current measurement is greater than the value of the first output). This is indicative of the attenuation of the current portion being much less than the attenuation of the prior portion of the object 102, causing the current value of the current output to be greater than the value of the prior output. Step 918 may be performed by the controller 24 by comparing the difference to a second threshold or range that is stored in the memory 25 to determine whether the absolute value of the measurement is greater than the threshold, for example.

If Yes, then the controller proceeds to Step 926 to decrease the energy and PRF. As discussed above with respect to Step 914, the determination to change the energy and the PRF may take place in different Steps. The controller 24 then stores the updated energy and PRF, in Step 930.

If it is determined in Step 918 that the difference is not "high-negative," the controller 24 proceeds to Step 920 to determine whether the difference is "low-negative," by determining whether the absolute value of the difference is less than the second threshold or range, for example. If Yes, then the controller 24 decreases the current value of the pulse width, in Step 928 and stores the pulse width in the memory 25, in Step 930.

When the leading edge of the current portion of the object 102 passes through the primary radiation beam 114, the controller 24 retrieves the stored values and causes the radiation source 104 to generate a primary radiation beam 114 to scan the portion of the object 102 at the stored values. The controller 24 determines when the current portion is passing through the primary radiation scanning beam 164 based on the known speed of relative movement between the object 102 and the radiation scanning system 100.

It is apparent that Steps 914-920 may be performed in a different order. It is also apparent that different tests may be performed to determine whether the dose should be increased or decreased when scanning a portion of the object 102 by the primary radiation beam 114. For example, the measurements may be compared directly to one or more thresholds, or ranges without comparing each measurement to a prior measurement.

Since the primary radiation beam 114 and the preview radiation beam 112 are formed simultaneously by the second collimator 106 from the same generator radiation beam 102, in one example, the characteristics of the preview beam will change when the characteristics of the primary radiation beam are changed. The value of the radiation detected by the preview detector may therefore differ based on the characteristics of the detected radiation beam, for adjacent portions of the object 102. It may therefore be advantageous to renormalize the thresholds/range based on the current dose and/or characteristics of the preview beam 112.

Renormalization may be provided by gain adjustment in the circuitry of the preview detector 118, 202, so that the threshold/range need not be changed. Alternatively, an offset may be provided to a set of thresholds to compensate for the change in dose. In another example, multiple sets of thresholds/ranges are stored in the memory 25 correlated to different doses and/or beam characteristics, so that the controller 24 can compare the detected values to the appropriate set based on the current dose and/or characteristics.

One of ordinary skill in the art will recognize that changes may be made to the embodiments described herein without departing from the spirit and scope of the invention, which is defined by the claims, below.

We claim:

1. A method of examining an object comprising:
scanning a portion of an object by a first radiation beam having a first value of a beam characteristic;
detecting the first radiation beam after interaction with the object by a first detector having a first resolution;
determining whether to change the first value of the beam characteristic to a second value different from the first value based, at least in part, on the first radiation beam detected by the first detector;
scanning the portion of the object by a second radiation beam having the first value or the second value of the beam characteristic based, at least in part, on the determination; and
detecting the second radiation beam after interacting with the object at a second location different from the first location, by a second detector having a second resolution greater than the first resolution.

2. The method of claim 1, further comprising:
selecting the second value of the beam characteristic based at least in part, on the detected first radiation beam.

3. The method of claim 1, further comprising:
moving the object with respect to the radiation source and the first and second detectors; or
moving the radiation source and the first and second detectors with respect to the object.

4. The method of claim 1, comprising:
generating a radiation beam; and
collimating the radiation beam by a collimator having a first slot to define the first radiation beam and a second slot to define the second radiation beam;
wherein the first slot is angled with respect the second slot and the first radiation beam is angled with respect to the second radiation beam, to scan the portion of the object by the first radiation beam before scanning the portion of the object by the second radiation beam.

5. The method of claim 1, wherein the beam characteristic comprises dose.

6. The method of claim 5, comprising changing the value of the dose by:
changing an energy, pulse repetition frequency, and/or a pulse width of the radiation beam; and/or
changing a value of a current of a charged particle beam injected into an accelerator to generate the radiation beam.

7. The method of claim 5, comprising:
scanning the portion of the object by a second radiation beam having a high dose if the detected first radiation beam has high attenuation; and
scanning the portion of the object by a second radiation beam having a low dose if the radiation detected by the first detector has low attenuation.

8. A method of examining an object comprising:
generating a radiation beam;
collimating the generated radiation beam to form a first radiation beam;
scanning a first portion of an object by the first radiation beam having a first value of a beam characteristic;
detecting the first radiation beam after interaction with the object;
determining whether to change the first value of the beam characteristic to a second value different from the first value based at least in part, on the detected first radiation beam;
collimating the generated radiation beam to form a second radiation beam at an angle with respect to the first radiation beam;
scanning the portion of the object by the second radiation beam with the first value or the second value based, at least in part, on the determination; and
detecting the second radiation beam after interacting with the object.

9. The method of claim 8, comprising:
collimating the generated radiation beam to form the first radiation beam by a first collimator defining a first slot to define the first radiation beam; and
collimating the generated radiation beam to form the second radiation beam by a second collimator defining a second slot to define the second radiation beam;
wherein the first slot is angled with respect to the second slot and the first radiation beam is angled with respect to the second radiation beam.

10. The method of claim 9, wherein the first slot extends only partially through the first collimator, to attenuate the first radiation beam.

11. The method of claim 8, further comprising:
determining a height of contents of the object based, at least in part, on the detected first radiation beam; and
collimating the generated radiation beam to define a height of a portion of the generated radiation beam prior to collimating the generated radiation beam, to define a height of the second radiation beam based, at least in part, on the determined height.

12. The method of claim 8, comprising:
detecting the first radiation beam by a first detector array having a first resolution; and
detecting the second radiation beam by a second detector array downstream of the first detector array, the second detector array having a second resolution greater than the first resolution.

13. The method of claim 8, wherein the beam characteristic comprises dose.

14. A radiation scanning system to examine objects, comprising:
a radiation source configured to generate radiation beams having a first value of at least one beam characteristic or a second value of the at least one beam characteristic different from the first value;
a first detector positioned at a first location to detect the first radiation beam after interacting with a portion of the object, the first detector having a first resolution;
a second detector positioned at a second location downstream of the first location to detect the second radiation beam after interacting with the object, the second detector having a second resolution greater than the first resolution; and
a controller configured to determine whether to change the first value of at least one of the at least one beam characteristic to the second value based, at least in part, on the first radiation beam detected by the first detector, when the portion is scanned by the second radiation beam.

15. The radiation scanning system of claim 13, further comprising:
at least one collimator defining a first slot to form a first radiation beam and a second slot to form the second radiation beam at an angle with respect to the first radiation beam.

16. The radiation scanning system of claim 15, further comprising:
a second collimator to define a height of the second radiation beam;
wherein the second collimator is between the radiation source and the at least one first collimator; or
the second collimator is between the at least one first collimator and the object.

17. The radiation scanning system of claim 14, wherein the first and second detectors comprise first and second detector arrays, respectively.

18. The radiation scanning system of claim 17, wherein:
the first and second detector arrays are part of a single detector array; and
the first detector array and the second detector array are separated by a space on the single detector array that does not include a detector array.

19. The radiation scanning system of claim 14, wherein the beam characteristic comprises dose.

20. The radiation scanning system of claim 19, wherein the radiation scanning system is configured to change the value of the dose by:
changing an energy, pulse repetition frequency, and/or pulse width of the radiation beam; and/or changing a value of the current of the charged particle beam injected into an accelerator to generate the radiation beam.

21. A radiation scanning system to examine objects, comprising:
a radiation source configured to generate radiation beams having a first value of at least one first beam characteristic and a second value of the at least one beam characteristic different from the first value;
a first collimator defining a first slot extending at least partially through the collimator to define a first radiation beam;
a second collimator defining a second slot to define a second radiation beam, wherein the first slot and the second slot are angled with respect to each other so that a portion of the object is scanned by the first radiation beam before being scanned by the second radiation beam;
a first detector positioned at a first location to detect the first radiation beam after interacting with the object;
a second detector positioned at a second location downstream of the first detector to detect the second radiation beam after interacting with the object; and
a controller configured to determine whether to change the first value of at least one of the at least one beam characteristic to the second value when the portion is scanned by the second radiation beam based, at least in part, on the first radiation beam detected by the first detector.

22. The radiation scanning system of claim 21, wherein:
the first detector has a first resolution and the second detector has a second resolution greater than the first resolution.

23. The radiation scanning system of claim 21, wherein:
the first and second detectors comprise first and second detector arrays;
the first and second detector arrays are part of a single detector array; and
the first detector array and the second detector array are separated by a space without a detector array.

24. The radiation scanning system of claim 21, further comprising:
a third collimator to define a height of at least the second radiation beam;
wherein the second collimator is between the radiation source and the at least one first collimator; or
the second collimator is between the at least one first collimator and the object.

25. The radiation scanning system of claim 24, wherein:
the first detector comprises a plurality of detector arrays having at least partially different vertical positions; and
at least some of the plurality of vertically extending detector arrays comprise a separate output.

26. The radiation scanning system of claim 21, wherein the beam characteristic comprises dose.

27. The radiation scanning system of claim 26, wherein the radiation scanning system is configured to change the value of the dose by:
changing a energy, pulse repetition frequency, and/or a pulse width of the radiation beam; and/or
changing a value of a current of a charged particle beam injected into an accelerator to generate the radiation beam.

28. The radiation scanning system of claim 21, wherein the first collimator and the second collimator are part of a single unit.

29. The radiation scanning system of claim 21, wherein the first collimator defines a first slot extending only partially through the first collimator.

* * * * *